United States Patent [19]

McCaffrey et al.

[11] Patent Number: 4,997,818
[45] Date of Patent: Mar. 5, 1991

[54] THERAPEUTIC METHOD FOR SELECTIVELY TREATING TERMINAL DEOXYNUCLEOTIDYL TRANSFERASE-POSITIVE NEOPLASTIC LEUKEMIAS AND LYMPHOMAS

[75] Inventors: Ronald P. McCaffrey, Needham, Mass.; Zachary Spigelman, Guilford, Conn.

[73] Assignee: The University Hospital, Boston, Mass.

[21] Appl. No.: 99,370

[22] Filed: Sep. 21, 1987

[51] Int. Cl.$^5$ .............................................. A61K 31/70
[52] U.S. Cl. ......................................... 514/45; 514/46; 514/47; 514/48; 514/49; 514/50; 514/51
[58] Field of Search ....................................... 514/45-51

[56] References Cited

U.S. PATENT DOCUMENTS

| 4,151,347 | 4/1979 | Umezawa et al. | 536/24 |
| 4,163,839 | 7/1979 | Umezawa et al. | 536/24 |
| 4,576,948 | 3/1986 | McCaffrey et al. | 514/908 |

FOREIGN PATENT DOCUMENTS

| 0206497 | 12/1986 | European Pat. Off. | 514/45 |
| 0018618 | 1/1982 | Japan | 514/50 |

OTHER PUBLICATIONS

CA:104:17020v, Matthes et al. (1986).
Wagar et al., The Chemical Abstracts, 102:39565n (1985).
Dahlberg et al., The Chemical Abstracts, 107: 17299e (1987).
Plunkett et al., The Chemical Abstracts, 83: 172430v (1975).
Tyrsted et al., The Chemical Abstracts, 68: 76681x (1968).
Herdewijn et al., J. Med. Chem. 30, pp. 1270-1278 (1987).

*Primary Examiner*—Johnnie R. Brown
*Assistant Examiner*—James O. Wilson
*Attorney, Agent, or Firm*—David Prashker

[57] ABSTRACT

A therapeutic method for specifically treating terminal deoxynucleotidyl transferase-positive neoplastic disease within living subjects is provided which is uniquely effective and selective. The therapeutic method comprises administering an effective concentration of a therapeutic composition to the subject, the therapeutic composition comprising a nitrogenous heterocyclic base selected from the group consisting of purines and purine derivatives and pyrimidines and pyrimidine derivatives; and a dideoxy-pentose monosaccharide moiety.

5 Claims, 3 Drawing Sheets

THERAPEUTIC METHOD FOR SELECTIVELY TREATING TERMINAL DEOXYNUCLEOTIDYL TRANSFERASE-POSITIVE NEOPLASTIC LEUKEMIAS AND LYMPHOMAS

FIELD OF THE INVENTION

The present invention is concerned with anti-cancer therapies which utilize selective DNA polymerase substrate analogues as the basis for treatment and is directed to specific means for selectively employing the activity of terminal deoxynucleotidyl transferase, the unique DNA polymerase of certain types of cancer cells as a therapeutic treatment.

BACKGROUND OF THE INVENTION

Historically, the present state of knowledge regarding DNA polymerases as a broad category of enzymes stems from the in-vitro synthesis of DNA first accomplished by Arthur Kornberg and his co-workers who in 1957 isolated an enzyme from *E. coli* bacteria now known as DNA polymerase I. This enzyme was found to catalyze the covalent addition of nucleotides to pre-existing DNA chains. Since the initial discovery of DNA polymerase I, a large number of different DNA polymerases have been isolated and characterized from different bacteria, viruses, and animal cells. Three different DNA polymerases (I, II, and III) have been identified and extensively studied in *E. coli* and *B. subtilius* bacterial strains. Investigations of many retroviruses has revealed the presence of RNA directed DNA polymerases, commonly termed "reverse transcriptases", which are presently thought to play a central role in the viral propagation of acquired immunodeficiency syndrome and feline leukemia. Such reverse transcriptases have been isolated from retrovirally infected cells of animals and humans as well.

Distinct from these are the three major DNA polymerases (alpha, beta, and gamma) which have been isolated from and identified in a variety of different eukaryotic cells. In eukaryotes, it is DNA polymerase alpha which is responsible for the replication of chromosomal DNA while polymerases beta and gamma synthesize other forms of DNA. More recently, a fourth DNA polymerase, termed delta, has been isolated from calf thymus and rabbit bone marrow but its significance is not yet known. In addition to these DNA polymerases in eukaryotes, there also exists terminal deoxynucleotidyl transferase whose presence is limited to primitive lymphocytes and to certain types of leukemia and lymphoma cells; and whose physiological function remains unknown. Clearly, there is a wide variety and diversity of enzymes which are recognized, characterized, and grouped under the broad category of DNA polymerases.

With the recognition of the variety and diversity of individual enzymes within the broad DNA polymerase category, the approach of selectively inhibiting individual DNA polymerases has been recognized and exploited not only for a definition of individual DNA polymerase function and activity but also as an effective means for therapeutically treating viral infections and neoplastic diseases and disorders [Plunkett and Cohen, *Cancer Research* 35:1547–1554 (1975); Major et al., *Biochemical Pharmacology* 31:2397 (1982); Kufe et al., *J. Biol. Chem.* 255:8997 (1980); Mitsuya and Broder, *Nature* 325:773–778 (1987)]. For some years, interest has been focused on the use of 2',3'-dideoxynucleotides such as 2',3'-dideoxyadenosine triphosphate (hereinafter "ddATP") and 2',3'-dideoxythymidine triphosphate (hereinafter "ddTTP") as compositions which differentially inhibit a variety of different eukaryotic and viral DNA polymerases [Toji and Cohen, *Proc. Natl. Acad. Sci. USA* 63:871–877 (1969); Toji and Cohen, *J. Bacteriol.* 103:323–328 (1970); Edenberg et al., *J. Biol. Chem.* 253:3273–3280 (1978); Allaudeen, H.S., *Biochem. Pharmacol.* 29:1149–1153 (1980); Krokan et al., *Biochemistry* 18:4431–4443 (1979); and Ono et al., *Biochem. Biophys. Res. Comm.* 88:1255–1262 (1979)]. Structurally, the 2',3'-dideoxynucleosides (hereinafter "ddNs") are analogues of the normal 2'-deoxynucleosides (hereinafter "dNs") which lack the 3'-OH group of the ribose sugar moiety. If the ddNs are phosphorylated to 2',3'-deoxynucleoside-5'-triphosphates (hereinafter "ddNTPs") or dideoxynucleotides, they become analogues of the 2'-deoxynucleoside-5'-triphosphates (hereinafter "dNTPs") which normally serve as substrates for cellular and viral DNA polymerases. Generally, however, it is agreed by investigators in this art that the rationale and the mechanism(s) of action by which specific DNA polymerases do or do not utilize one or more ddNTPs as substrate analogues is not clear or understood; and that there is no predictive value or expectation that specific dideoxynucleoside or dideoxynucleotide would be recognized by any individual DNA polymerase [Wagar et al., *J. Cell. Physiol.* 121:4022–408 (1984) and the references cited therein].

This lack of predictive expectations is well demonstrated by the recent intensity and focus on the use of 2',3'-dideoxynucleotides as anti-retroviral agents, particularly with regard to HIV (HTLV-III/LAV) infections and acquired immunodeficiency syndrome or AIDS. The retroviral reverse transcriptases, the viral DNA polymerases, are able to utilize the triphosphorylated dideoxynucleosides (ddNTPs) as substrate analogues—the consequence of which is that further nucleotide addition becomes impossible due to the absence of a 3'-OH group on the ribose moiety. Through this technique of chain termination, proviral DNA synthesis is prevented and retroviral proliferation is inhibited [Mitsuya and Broder, *Nature* 325:773–778 (1987); Balzarini et al., *Biochem. Biophys. Res. Comm.* 140:735–742 (1986); Mitsuya and Broder, *Proc. Natl. Acad. Sci. USA* 83:1911 (1986); Mitsuya et al., *Proc. Natl. Acad. Sci. USA* 82:7096 (1985); Smoler et al., *J. Biol. Chem.* 246: 7697 (1971); Sanger et al., *Proc. Natl. Acad. Sci. USA* 74:5463 (1977)].

In comparison to other members of the DNA polymerase category, terminal deoxynucleotidyl transferase (hereinafter "TdT") has remained a relatively unknown and uncharacterized enzyme. Although the existence of TdT has been known for twenty-five years, its physiological function in the cells in which it is expressed, whether normal or malignant, remains unknown. Terminal deoxynucleotidyl transferase, however, has been demonstrated to be a unique DNA polymerase which catalyzes the polymerization of deoxyribonucleotides on the 3'-hydroxyl ends of preformed oligo- or polydeoxynucleotide initiators, in a template independent manner [Bollum, F.J., in *The Enzymes: Terminal Deoxynucleotidyl Transferase* (R.D. Boyer, editor), Academic Press Inc., New York, 1974, p 145]. Its expression is restricted, in normal animals, to subsets of primitive lymphocytes and, in disease states, to the blast cells of certain forms of acute leukemia and diffuse lymphoma

[McCaffrey et al., *Cancer Research* 41:4814 (1981)]. For immunobiologists, TdT has emerged as a useful marker for characterizing subsets of pre-B lymphocytes and pre-T lymphocytes [Silverstone et al., *J. Exp. Med.* 144:453 (1976); Janossy et al., *J. Immunol.* 123:1525 (1979); Bollum, F.J., *Blood* 54:1203 (1979); Blatt et al., *NEJM* 303:918 (1980); Greaves, M.F., *Cancer Research* 41:4752 (1981)]. For physicians clinically treating leukemias and lymphomas, neoplastic cell TdT status has become a useful criterion for patient assignment to therapeutically meaningful categories [Marks et al., *NEJM* 298:812 (1978)].

Due to the presence of terminal deoxynucleotidyl transferase in some leukemias and lymphomas, a strategy for the treatment of such diseases using specific inhibitors of TdT has been suggested and empirically attempted. To date, such investigations have focused on the use of 6-anilinouracil derivatives as both specific compositions and selective methods for inhibiting the activity of terminal deoxyribonucleotidyl transferase [McCaffrey et al., in *New Experimental Modalities In The Control Of Neoplasia* (P. Chandra, editor), NATO ASI Series A, Life Sciences Volume 120, 1986, page 213; U.S. Pat. No. 4,576,948]. These studies have established that TdT is important for the viability of the cells in which it is expressed: the inhibition of TdT by 6-anilinouracils results in cytotoxic damage to TdT-positive cells. However, 6-anilinouracils are not readily soluble except in dimethylsulfoxide, a circumstance which inhibits their clinical utility. Moreover, in light of the dismal prognosis for patients afflicted with TdT-positive diseases (typically, only several months), there remains a continuing need for therapeutically effective compositions in the treatment of human leukemias and lymphomas using TdT as a therapeutic target. Accordingly, the development of additional therapeutic compositions which would selectively eliminate TdT-positive neoplastic cells would be recognized as a major advance and welcome improvement upon the presently available means for therapeutic treatment for TdT-positive leukemias and lymphomas.

SUMMARY OF THE INVENTION

The present invention provides a therapeutic method for selectively treating terminal deoxynucleotidyl transferase positive neoplastic disease in a living subject comprising the steps of:

administering to the subject an effective concentration of a therapeutic composition comprised of (a) a nitrogenous heterocyclic base selected from the group consisting of purines and purine derivatives, and pyrimidines and pyrimidine derivatives; and (b) a dideoxypentose, monosaccharide moiety.

The therapeutic composition may further comprise a molecule of phosphoric acid covalently bound to the deoxyribose moiety. The therapeutic composition may be administered by a variety of different routes and should be provided in quantities such that a concentration ranging from 50-150 micromoles per milliliter of plasma is achieved and maintained for several hours in the subject after administration.

DETAILED DESCRIPTION OF THE DRAWINGS

The present invention may be more fully and easily understood when taken in conjuction with the accompanying drawings, in which.

DETAILED DESCRIPTION OF THE PREFERRED EMBODIMENTS

Figure 1:
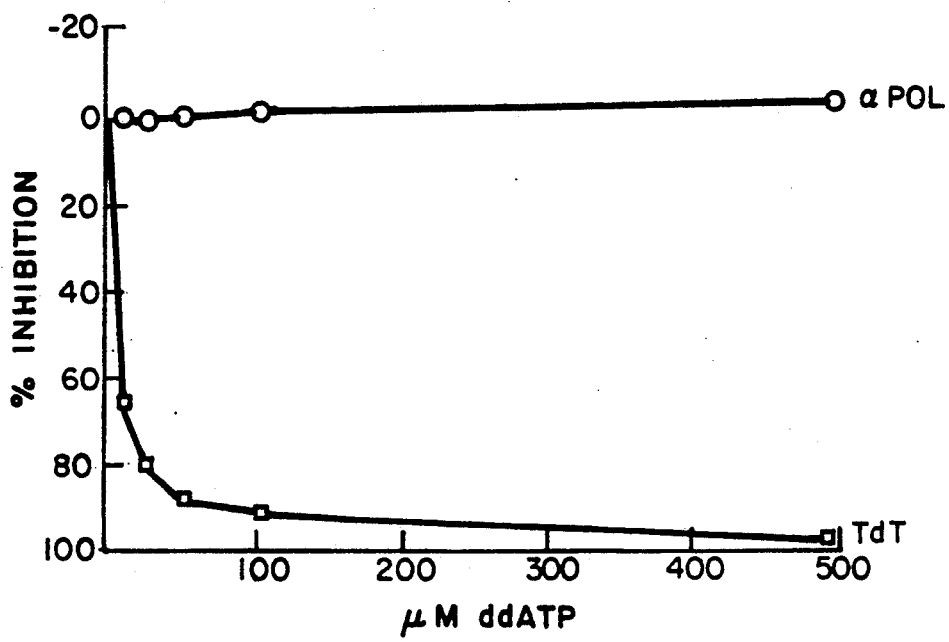
FIG. 1 is a graph illustrating the effect of 2', 3'-dideoxyadenosine triphosphate on DNA polymerase alpha and terminal deoxynucleotidyl transferase.

The present invention is a therapeutic method for specifically treating a living subject afflicted with terminal deoxynucleotidyl transferase (hereinafter "TdT")—positive neoplastic cells using 2', 3'-deoxynucleosides (hereinafter "ddNs") as substrate analogues which inhibit the formation of nascent DNA by the process of chain terminating additions. The present invention employs ddNs or 2', 3'-dideoxynucleoside monophosphates (hereinafter "ddNMPs") as therapeutic compositions which are administered to the subject in a concentration which is effective to provide a range of 50-150 micromoles (hereinafter "uM") per milliliter (hereinafter "ml") of plasma for several hours duration, preferably about 6 hours. Once administered, the ddNs and ddNMPs are converted intracellularly into triphosphorylated 2', 3'-dideoxynucleotides (hereinafter "ddNTPs") which, after addition by TdT to 3' sites in nascent DNA, prevent further nucleotide addition due to the absence of a 3'-OH group on the ribose moiety of the incorporated ddNMP. Through this process of chain termination, authentic DNA synthesis by TdT is prevented, which ultimately results in cell death.

The present invention is based upon two novel observations: First, that the unique DNA polymerase of primitive lymphocytes, terminal deoxynucleotidyl transferase, recognizes and accepts ddNTPs as substrate analogues for end-addition synthesis reactions, while the major mammalian replicative polymerase, DNA polymerase alpha, does not recognize and does not employ ddNTPs as substrate analogues for DNA synthesis. Second, TdT-positive cells are killed upon exposure to ddA, a representative ddN which is the non-phosphorylated precursor of ddATP. In contrast, TdT-negative cells are not affected by ddA. This differential specificity and sensitivity to ddNs provides a means for selective killing of TdT-positive neoplastic cells.

The compositions provided for effective therapeutic administration to a subject afflicted with TdT-positive neoplastic cells comprises, at a minimum, (a) a nitrogenous heterocyclic base selected from the group consisting of purines and purine derivatives, and pyrimidines and pyrimidine derivatives, and (b) a dideoxy-pentose sugar. It will be appreciated and understood that both naturally occuring and chemically synthesized purines, purine derivatives, pyrimidines, and pyrimidine derivatives may be utilized. A non-exhaustive, but representative listing of such nitrogenous heterocyclic bases is provided by Table I.

TABLE I

| PURINES | PYRIMIDINES |
|---|---|
| Adenine (6-aminopurine) | Cytosine (4-amino-2-oxopyrimidine) |
| Guanine (2-amino-6-oxopurine) | Thymine (5-methyl-2,4,-dioxopyrimidine) |
| $N^6$-Methyladenine | Uracil (2,4-dioxopyrimidine) |
| 2-Methylguanine | 5-Methylcytosine |
| 1-Methyladenine | 5-Hydroxymethylcytosine |
| 2-Methyladenine | $N^4$-Acetylcytosine |
| 7-Methyladenine | 3-Methylcytosine |
| $N^6,N^6$-Dimethyladenine | 5,6-Dihydrouracil |
| $N^6$-(2-Isopentenyl)adenine | 1-Methyluracil |
| 1-Methylguanine | 3-Methyluracil |
| 7-Methylguanine | 5-Hydroxymethyluracil |
| $N^2$-Methylguanine | 2-Thiouracil |
| $N^2,N^2$-Dimethylguanine | |

For definitional purposes, however, structural formulas of useful purines, pyrimidines and their respective derivatives are also included herein. Formulation I defines purines and purine derivatives as:

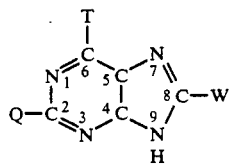
(I)

wherein Q, T, and W are selected from the group consisting of H, NH₂, O, and NHR where R is an alkyl, aryl, or aromatic group.

Similarly, structural Formula II provides a definition of pyrimidines and pyrimidine derivatives in the form of:

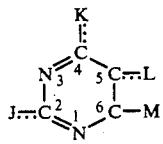
(II)

wherein J, K, M and L are selected from the group consisting of H, NH₂, O, and R', NHR', and R'OH where R' is an alkyl, aryl, or aromatic group.

The dideoxyribose moiety component of the therapeutic composition comprises the preferred embodiment of this component in the therapeutic composition to be administered. It will be recognized, however, that any dideoxypentose monosaccharide derivative lacking an hydroxyl group on the 2'- and 3'-carbon atoms is also suitable for use. The dideoxypentose monosaccharides moieties thus include both the linear pentose sugar derivatives of arabinose, ribose, lyxose, and xylose; but also the branched chain pentose derivatives of apiose, hamanelose, streptose, cordycepose, and the like. Clearly, while the linear dideoxypentose sugars are preferred, it is expected that branched dideoxypentose sugar derivatives will be effective in some measureable degree.

In some alternate embodiments of the therapeutic compositions to be administered, a single molecule of phosphoric acid is covalently bonded to the 5'-carbon atom of the dideoxypentose sugar as a monophosphate group. It is expected that the presence or absence of the monophosphate group within the therapeutic composition will not markedly effect the efficacy of the therapeutic method comprising the present invention.

The therapeutic compositions described herein are to be administered to the subject in effective concentrations such that a range of 50–150 uM of ddN or ddNMP is present per milliliter of plasma for several hours duration, preferably about 6 hours. In human subjects, a preferred effective concentration after administration ranging from 50–100 uM is desireable. In extreme cases or in other animal subjects, an upper effective limit of 100–150 uM per milliliter of body fluid is expected to be therapeutically effective. Concentrations of ddN or ddNMP greater than these ranges (after administration) may result in cytotoxicity to normal cells in the host due to excess accumulations of nucleosides intracellularly. This causes a cytotoxicity which is indiscriminate and non-selective.

The route of administration to the intended subject of one or more therapeutic compositions may be chosen to accommodate the needs of the patient and his/her particular disorder. The therapeutic compositions are generally soluble in water at neutral or alkaline pH levels. The effectiveness of the composition may be substantially reduced or entirely destroyed at low pH levels such as are found in the stomach. Accordingly, if the therapeutic agent is to be given orally, the composition should be formulated as an enteric coated capsule which would prevent destruction of the therapeutic composition and allow its passage into the intestines of the subject where it may be properly assimilated into the body. If the route of administration is to be parenteral, as by intravenous, intramuscular, cutaneous, or subcutaneous injection, it is expected that each therapeutic composition will be prepared in sterile form; in multiple or single dose formats; and dispersed in a suitable fluid carrier such as sterile physiologic saline or a 5% dextrose solution commonly used with injectables. Alternatively, the therapeutic composition can be dispersed into suitable oil emulsions for use in suppository form. Sublingual administration is also expected to be useful for effective delivery of the therapeutic compositions.

As will be empirically demonstrated hereinafter, a ranking order of efficiency of the various ddNTPs as competitive substrate analogues for TdT exists. The ranked order of competitiveness is: dideoxyadenosine triphosphate (hereinafter "ddATP"); which is more effective than dideoxyguanosine triphosphate (hereinafter "ddGTP"); which is more effective than dideoxyinosine triphosphate (hereinafter "ddITP"); which, in turn, is more effective than dideoxycytosine triphosphate (hereinafter "ddCTP"); which is more effective than dideoxythymidine triphosphate (hereinafter "ddTTP"). It is conventionally recognized that inosine is a deaminase enzyme reaction product of adenosine, a degradation which can be inhibited via the inclusion of purine deaminase inhibitors such as coformycin (hereinafter "CF"). As empirically demonstrated hereinafter, the cytotoxicity of TdT-positive cells is enhanced when CF is administered prior to the dideoxyadenosine (hereinafter "ddA"). Accordingly, it is preferred that the therapeutic method employ concomitant use of a dideoxypurine and a purine deaminase inhibitor such as coformycin. A representative useful treatment comprises 100 uM ddA and 30 uM CF concurrently. Alternatively, an effective range of CF from 10–50 uM per 100 uM of ddA may be usefully employed.

The present invention is an efficacious therapeutic treatment for TdT-positive neoplastic cells generally as these are found in-vivo. TdT-positive neoplastic cellular diseases and disorders include a large variety of leukemias and lymphoblastic lymphomas. A representative listing of pathological disorders which have been evaluated upon a case basis for the presence of TdT is provided by Table II below.

TABLE II

| CLINICAL DIAGNOSIS | TOTAL NUMBER OF CASES | NUMBER OF TdT-POSITIVE CASES |
| --- | --- | --- |
| Acute lymphoblastic leukemia | 300 | 290 |
| Acute myeloblastic leukemia | 120 | 10 |
| Acute undifferentiated leukemia | 30 | 16 |
| Blastic chronic myelogenous leukemia | 100 | 38 |
| Post-polycythemia vera leukemia | 15 | 3 |
| Post-myeloid metaplasia leukemia | 16 | 10 |
| Post-chemo/radiotherapy leukemia | 9 | 2 |
| Stable phase chronic myelogenous leukemia | 30 | 0 |
| B-cell chronic lymphocytic leukemia | 15 | 0 |
| T-cell chronic lymphocytic leukemia | 3 | 0 |
| Sezary syndrome | 6 | 0 |
| Hairy cell leukemia | 9 | 0 |
| Multiple myeloma | 7 | 0 |
| Hodgkin's disease | 7 | 0 |
| Lymphoblastic lymphoma | 15 | 15 |
| Nodular lymphoma | 6 | 0 |
| Diffuse, poorly differentiated lymphocytic lymphoma | 9 | 0 |
| Diffuse histiocytic lymphoma | 6 | 0 |

To demonstrate the utility, specificity, and efficacy of the therapeutic methodology comprising the present invention, a variety of experiments and empirical data will be described hereinafter. It will be expressly understood, however, that these empirical results are merely descriptive of the present invention as a whole; and serve to merely illustrate specific instances and situations in which the present invention may be usefully employed. None of the experimental modes, empirical data, or conclusions are deemed to be restrictive of the invention in any form or use; to the contrary, it will be recognized that these experiments merely demonstrate the range of applications and the effective parameters one may expect to be in effect when employing the present invention.

EXPERIMENTAL SERIES 1

Initially, the effect of various ddNTPs on TdT and DNA polymerase alpha was evaluated. DNA polymerase alpha, purified from calf thymus according to Kornberg [*DNA Replication*, W.H. Freeman and Company, 1980, p 206] and Wahl et al. [*Biochemistry* 23:1895 (1984)] was purchased from Pharmacia, Inc. (Piscataway, N.J.). TdT, purified from calf thymus, was purchased from DuPont/NEN Products, Boston, Massachusetts). Enzyme assays were conducted at 37 C. under conditions established to be optimal for each assay. For DNA polymerase$\alpha$, 0.1 ml of reaction mixture contained: 0.05 M tris-HCl (pH 8.3); 4 mM dithiothreitol; 4 mM MgCl; 10 ug poly(dAT); 0.05 mM $^3$H-dATP; 0.05 mM dTTP; and 0.05 units of enzyme. For TdT assays, 0.1 ml of standard reaction mixture contained: 0.05 M tris-HCl (pH 8.3); 2 mM dithiothreitol; 0.6 mM MnCl; 20 ug oligo(dA) 50; 0.1 mM $^3$H-dGTP; and 0.5 units of TdT.

For these studies, ddNTPs were dissolved in deionized distilled water and added to the respective reaction mixtures at time zero to give the effective final concentrations. The degree of reaction or inhibition was calculated from simultaneous control reactions. The mode of inhibition and inhibition constants were determined using Linweaver-Burke and Dixon plots. Each of the respective reactions was stopped using 0.5 ml of cold (4 C) 0.1 M sodium pyrophosphate containing 1 mg/ml yeast RNA (hereinafter "NaPP") and precipitated with 0.5 ml of cold 25% trichloroacetic acid (hereinafter "TCA"). The precipitates centrifuged at 13,000$\times$gravity in a microfuge for one minute; resolubilized in 0.2 ml of 0.3M NaOH; and then reprecipitated with NaPP and TCA. Following a second 0.3 M NaOH resolubilization, 10 ml of scintiverse II (Fisher Scientific Company, Fairlawn, N.J.) was added to each sample for counting in a Beckman LS3700 liquid scintillation counter.

It should be noted also that for certain TdT assays, a variety of different initiators were used in place of oligo (dA) 50. These included: activated DNA; 5'-$^{32}$T-GTCCGTCTCTGCCTC-3' (15 MER synthesized on an automated synthesizer using standard phosphoramidite chemistry having a $^{32}$P-end labeled by a standard Maxam-Gilbert reaction); YEP-FG-2-plasmid DNA; oligo (dC) 18; oligo (dT) 18; and various $^3$H-substrates such as dCTP, dATP, and dTTP in place of $^3$H-dGTP. Reactions utilizing the 15 MER initiator contained either 5 mM MgCl$_2$ or 1 mM CoCl$_2$ in place of MnCl$_2$.

The effect of ddATP on DNA polymerase alpha and TdT is illustrated by FIG. 1. Both enzymes were assayed as described previously herein. Each ddATP point represents the mean of triplicate determinations expressed as a percentage of simultaneously run control reactions. As illustrated by FIG. 1 the addition of micromolar concentrations of ddATP to a TdT polymerization reaction system dramatically inhibits the incorporation of the authentic dATP nucleoside substrate. In comparison, DNA polymerase alpha does not recognize ddATP. It should be noted also that the use of other ddNTPs under identical test conditions similarly did not affect the enzyme activity of DNA polymerase alpha; in comparison, there was a ranking order of comparative efficiency for various ddNTPs and 3'-azido thymidine triphosphate (hereinafter "AZTTP"). Using the various ddNTPs and AZTTP concentrations producing 50% inhibition of $^3$H-dGTP incorporation in the standard TdT assay, a ranked order of competitiveness was established which is provided by Table III below. It will be noted that the mode of inhibition by the ddNTPs is competitive with respect to the authentic substrate, dGTP, and is non-competitive with respect to the initiator employed. Moreover, the competitive ranking order of Table III is neither initiator nor substrate dependent. The value of this ranking order becomes most appreciated when it is recognized that DNA polymerase alpha was not inhibited by any of these ddNTps at any concentration up to 500 uM.

TABLE III

| SUBSTRATE ANALOGUE | CONCENTRATION OF ddNTP PRODUCING 50% INHIBITION OF 3H-dGMP INCORPORATION |
| --- | --- |
| ddATP | 9.0 μM |
| ddGTP | 18.0 μM |

TABLE III-continued

| SUBSTRATE ANALOGUE | CONCENTRATION OF ddNTP PRODUCING 50% INHIBITION OF 3H-dGMP INCORPORATION |
|---|---|
| ddITP | 20.0 μM |
| ddCTP | 24.8 μM |
| ddTTP | 47.2 μM |
| AZTTP | 133.0 μM |

Figure 2:
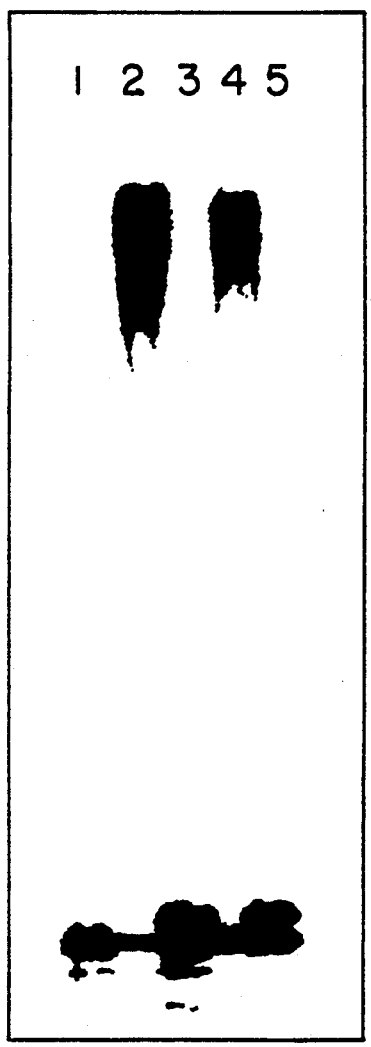
FIG. 2 is an autoradiograph demonstrating the effect of 2', 3'-dideoxyadenosine triphosphate as a chain terminator.

It should be noted that the mechanism of inhibition by any of the ddNTPs upon TdT catalysis is by chain termination. This is demonstrated by the autoradiograph illustrated by FIG. 2 which demonstrates ddATP as a chain terminator. A radiolabelled oligomer ($^{32}$P-GTCCGTCTCTGCCTC-3') shown in Lane 1 was used as an initiator for TdT-catalyzed polymerization using: dATP (Lanes 2 and 4); or ddATP (Lanes 3 and 5) as substrates. Lanes 2 and 3 represent the reaction products generated in the presence of MgCl$_2$ while Lanes 4 and 5 represent the reaction products generated in the presence of CoCl$_2$ respectively. Each reaction product was electrophoresed on a 20% polyacrylamide gel under denaturing conditions (2.5 hours at 35 watts, 2800 volts). The results illustrated by FIG. 2 demonstrate the retarded migration of the TdT catalyzed reaction product using the authentic substrate dATP following multiple nucleotide additions to the pre-formed radiolabeled oligomer (Lanes 2 and 4). In comparison, when ddATP is used, only one residue is added by the TdT (Lanes 3 and 5). Thus, the effectiveness of chain termination by ddATP is clearly established.

EXPERIMENTAL SERIES 2

To determine the effect of TdT catalyzed ddAMP chain terminating insertions within intact cultured cells, a series of TdT-positive and TdT-negative cells were exposed in-vitro to ddA, the non-phosphorylated precursor of the most efficient competitive substrate analogue, ddATP. ddA can enter intact cells whereas ddATP cannot; and, once having entered the cell, ddA can be successively phosphorylated into ddATP. Accordingly, a variety of cell lines from different sources and representative of different neoplastic disorders were evaluated. The listing of cells employed is provided by Table IV below.

TABLE IV

| CELL LINE | SOURCE/TYPE | TdT STATUS |
|---|---|---|
| B-244 | Murine lymphoid cells | Positive |
| 298-26 | Murine lymphoid cells | Positive |
| MOLT-4 | Human leukemia cells | Positive |
| NALM-6 | Human leukemia cells | Positive |
| HPB-ALL | Human leukemia cells | Positive |
| CEM | Human leukemia cells | Positive |
| 8402 | Human leukemia cells | Positive |
| H9 | Human lymphoid cells | Negative |
| ML3 | Human leukemia cells | Negative |
| 8392 | Human leukemia cells | Negative |
| HeLa | Human cervical carcinoma cells | Negative |
| K562 | Human leukemia cells | Negative |
| NIH-3T3 | Murine fibroblast cells | Negative |

Each cell line was utilized in exponential growth phase. For test purposes, cells were seeded at 3×10 cells/ml in T25 flasks containing 4 ml of culture medium. Cell counts were made using a hemocytometer. Cell viability was determined using the tryptan blue dye exclusion method. The degree of growth inhibition was calculated by comparison with untreated controls.

Initially, the effect of a 48 hour continuous exposure to 250 uM and 500 uM of ddA upon four TdT-positive and three TdT-negative cell lines was evaluated. The results are summarized within Table V.

TABLE V

| CELL LINE | TdT STATUS | % GROWTH INHIBITION AT 250 μM | % GROWTH INHIBITION AT 500 μM |
|---|---|---|---|
| MOLT-4 | Positive | 60% | 92% |
| NALM-6 | Positive | 30% | 95% |
| 298-26 | Positive | 80% | 99% |
| HPB-ALL | Positive | 40% | 99% |
| L1210 | Negative | 15% | 50% |
| ML3 | Negative | 0% | 40% |
| 8392 | Negative | 0% | 0% |

The growth inhibition data of Table V is defined as the ratio of viable cells in the ddA exposed cultures in comparison to control cultures. Each determination reflects the mean of triplicate flasks. It is noted that at 250 uM of ddA, there was marked growth inhibition (30–80%) in all four TdT-positive cell lines whereas there was very little effect among the TdT-negative cells (0–15% growth inhibition). At 500 uM of ddA, the cytotoxicity in the TdT-positive lines was further increased (92–99% growth inhibition). At this concentration level, 2 of the 3 TdT-negative lines also show measureable growth inhibition (40–50%). This is attributed to selective purinogenic cytotoxicity which is also exhibited by the authentic substrate, deoxyadenosine, at this concentration.

As a result, another series of experiments was conducted in which the non-selective purinogenic cytotoxicity was reduced. In this experimental series, a variety of different cell lines were pre-incubated for 30 minutes with the adenosine deaminase inhibitor, coformycin (CF). This CF exposure was then followed by a continuous 48 hour exposure to 250 uM ddA with suitable controls. Growth inhibition was defined as the ratio of viable cells in the CF/ddA exposed cell cultures in comparison to control cultures. Each determination reflects the mean of quadruplicate flasks. The results are provided by FIG. 3 and Table VI respectively.

TABLE VI

| LYMPHOID | TdT STATUS | % GROWTH INHIBITION |
|---|---|---|
| NALM-6 | Positive | 95% |
| MOLT-4 | Positive | 85% |
| CEM | Positive | 85% |
| 298-26 | Positive | 95% |
| B-244 | Positive | 95% |
| 8402 | Positive | 80% |
| HPB-ALL | Positive | 95% |
| H9 | Negative | 20% |
| ML3 | Negative | 0% |
| 8392 | Negative | 0% |

| NON-LYMPHOID | TdT STATUS | % GROWTH INHIBITION |
|---|---|---|
| HeLa | Negative | 20% |
| 3T3 | Negative | 0% |
| K562 | Negative | 0% |

Figure 3:
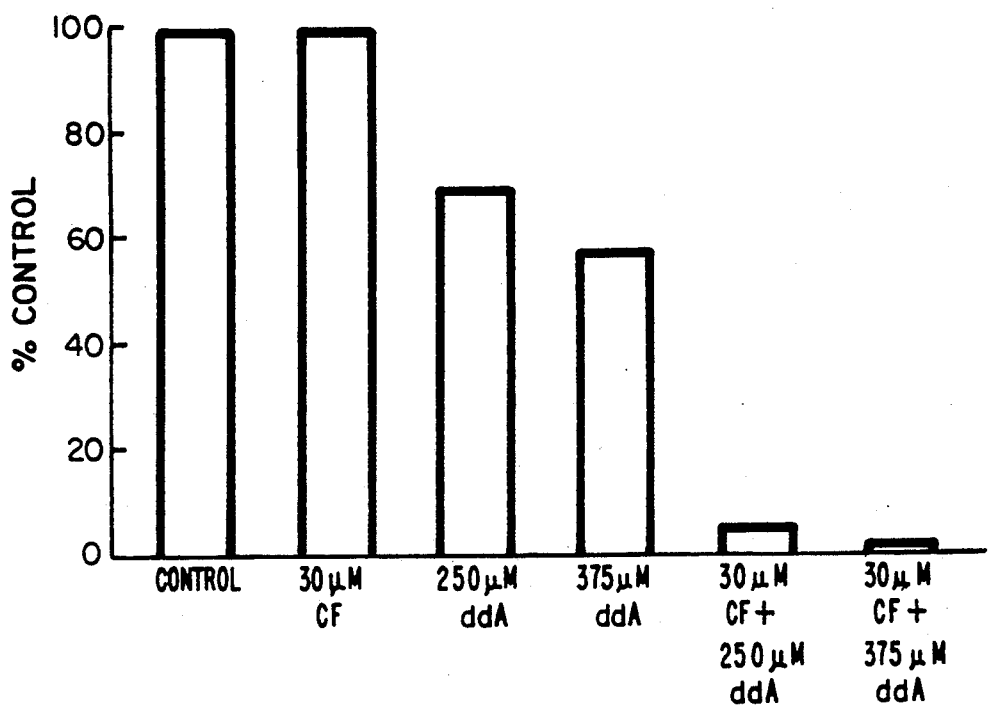
FIG. 3 is a graph illustrating the effects of a thirty minute preincubation with the adenosine deaminase inhibitor, coformycin and 2', 3'-dideoxyadenosine on TdT positive NALM6 cells in culture.

The data of FIG. 3 represents the effect of CF and ddA on TdT-positive NALM-6 cells in culture. As illustrated, the NALM-6 cells are extraordinarily sensitive to the preincubation with 30 uM CF and 250 uM of ddA (90% growth inhibition). In comparison, the data of Table VI summarizes the results from similar experiments utilizing six other TdT-positive and six TdT-negative cell lines. All the TdT-positive cell lines tested (seven in total number) resulted in major (80-95%) growth inhibition at 48 hours exposure to 250 uM ddA preceeded by the 30 minute exposure to 30 uM CF. Among the six TdT-negative cell lines, only two (the HeLa and H9 cells) were affected at 48 hours (20% growth inhibition). The data clearly demonstrates that ddA and CF in combination are synergistically cytotoxic for TdT-positive lymphoid cells.

EXPERIMENTAL SERIES 3

To further demonstrate the cytotoxic effects of ddA and CF in combination, mutant cell lines of the TdT-positive cell line CEM were utilized. The CEM cell line is an established TdT-positive line derived from human leukemia cells. The CEM Ara-C line is a mutant human T-lymphoblastoid cell line derived from the parent line CEM-CCRF; and is a cell line efficient in deoxycytidine kinase, an enzyme responsible for the bulk of intracellular ddA phosphorylation [Hershfield et al., *J. Biol. Chem.* 257:6380–6386 (1982)]. The CEM-TUB-4C line is a CEM mutant which is deficient in nucleoside transport across cell membranes [Kang and Kimball, *Cancer Research* 44:461 (1984)]. All the parent and mutant CEM cell lines are TdT-positive cells as evidenced by biochemical assay.

Figure 4:
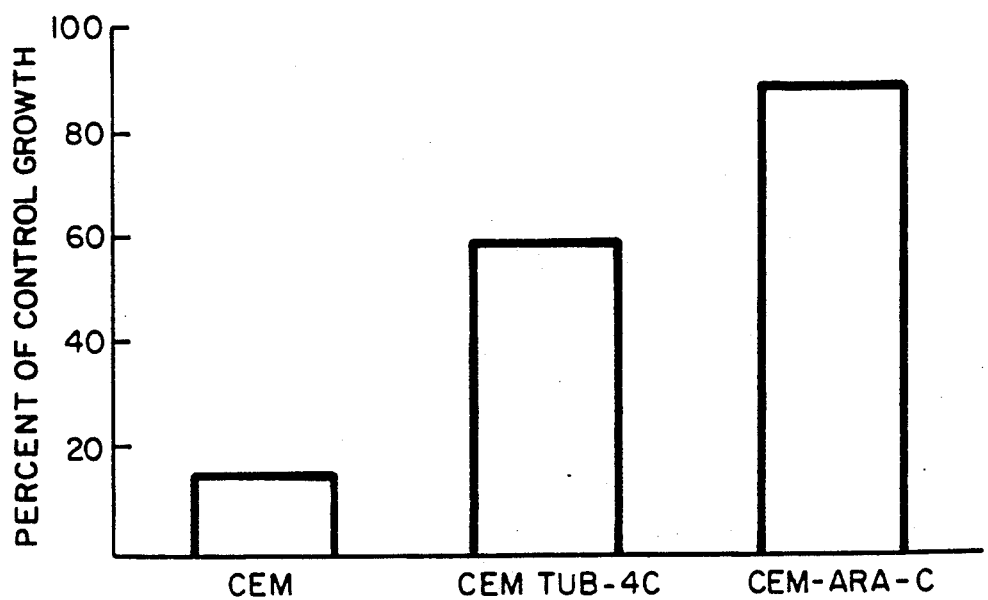
FIG. 4 is a graph illustrating the effects of 2', 3'-dideoxyadenosine and coformycin on wild type CEM cells and mutant CEM cell lines.

Experimentally, wild type CEM cells, CEM Ara-C cells, and CEM-TUB-4C cells were continuously exposed to 250 uM of ddA and 30 uM of CF for 48 hours. The results are illustrated by FIG. 4 in which the data are expressed as a percent of controlled growth for each cell line. Each determination represents the mean result of six flasks.

The data demonstrates that wild type CEM cells are 85% growth inhibited. In comparison, the CEM-TUB-4C (transporter deficient) cells are only 40% growth inhibited while the CEM Ara-C (kinase deficient) cells are almost totally resistant to the effects of ddA and CF in combination. This data is entirely consistent with the view that ddATP is the moiety mediating the cytotoxicity in TdT-positive tumor cells.

EXPERIMENTAL SERIES 4

To further demonstrate the specificity of the present invention for TdT-positive cells, a series of experiments were conducted using vectored cell lines. PD-31 is a murine Abelson-virus infected leukemia cell line which actively rearranges its kappa-immunoglobulin light chain genes [Lewis et al., *Cell* 30:807-816 (1982)]. The parent PD-31 cell is a pre-B cell which is demonstrably TdT-negative. The parent cell line can be rendered TdT-positive by transfection with a DOL-HMI retroviral vector which contains a human-murine TdT-cDNA construct. TdT transcription and expression can be confirmed by Northern blotting and biochemical enzyme assay. The transfected cell line, PD-31-DOL-HMI remains TdT-positive and may be cultured in RMPI-1640 medium supplemented with 10% fetal calf serum (hereinafter "FCS").

Figure 5:
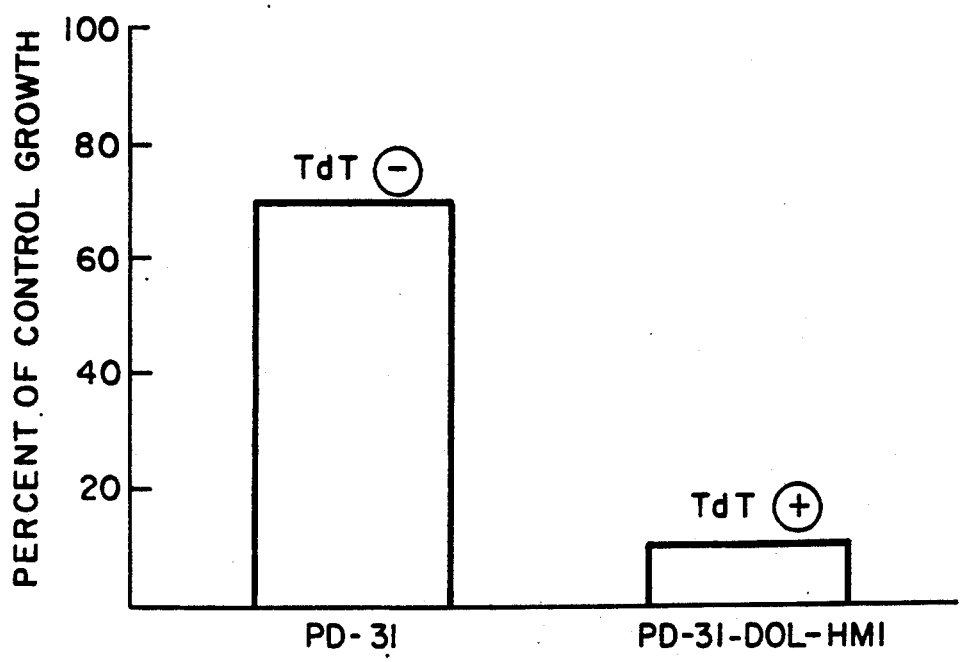
FIG. 5 is a graph illustrating the effects of 2', 3'-dideoxyadenosine and coformycin upon TdT-positive and TdT-negative PD-31 cell lines.

Experimentally, parent PD-31 cells (TdT-negative) and PD-31-DOL-HMI (TdT-positive) cells were exposed to 30 uM of CF for 30 minutes and then continuously exposed to 250 uM of ddA for 48 hours. The results are illustrated by FIG. 5. Each result is expressed as percent of control growth for each cell line. Each determination represents the mean of triplicate flasks.

As shown by FIG. 5, the PD-31 cells are 30% growth inhibited by the ddA and CF in combination. In comparison, the PD-31-DOL-HMI cells rendered artificially TdT-positive reveals a significant increase in sensitivity to ddA and CF in combination; there is a 90% growth inhibition after 48 hours. This data clearly demonstrates the specificity of the present therapeutic methodology for TdT-positive cells.

EXPERIMENTAL SERIES 5

Finally, a series of experiments were conducted to demonstrate the efficacy of the present invention upon clinical samples obtained from living human patients afflicted with acute leukemia. Leukemic blast cells from bone marrow or peripheral blood were obtained from 12 patients; of these, six persons were diagnosed as afflicted with acute lymphatic leukemia; three persons were diagnosed as afflicted with acute myeloblastic leukemia; two persons were diagnosed as afflicted with blastic chronic myelogenous leukemia; and one person was diagnosed as having acute myelogenous leukemia, complicating multiple myeloma. These diagnoses were based upon standard clinical and laboratory criteria. In ten of these twelve patients, blast cells constituted more than 75% of the mononuclear cells. In the eleventh and twelfth patients, 32% and 42% of the mononuclear cells were blast cells.

The leukemic cells from each person were enriched on Ficoll-Hypaque medium; washed in phosphate-buffered saline without divalent cations; resuspended in RPMI-1640 medium containing 20% FCS; and then grown in RPMI-1640 media supplemented with 10% FCS. The TdT status of each cell sample was independently determined by conventional biochemical assay before culturing. The assay results revealed that six cell samples were TdT-negative blast cells while six individual cell samples revealed themselves to be TdT-positive leukemic blast cell cultures. The six TdT-positive cases all had acute lymphoblastic leukemia.

Figure 6:
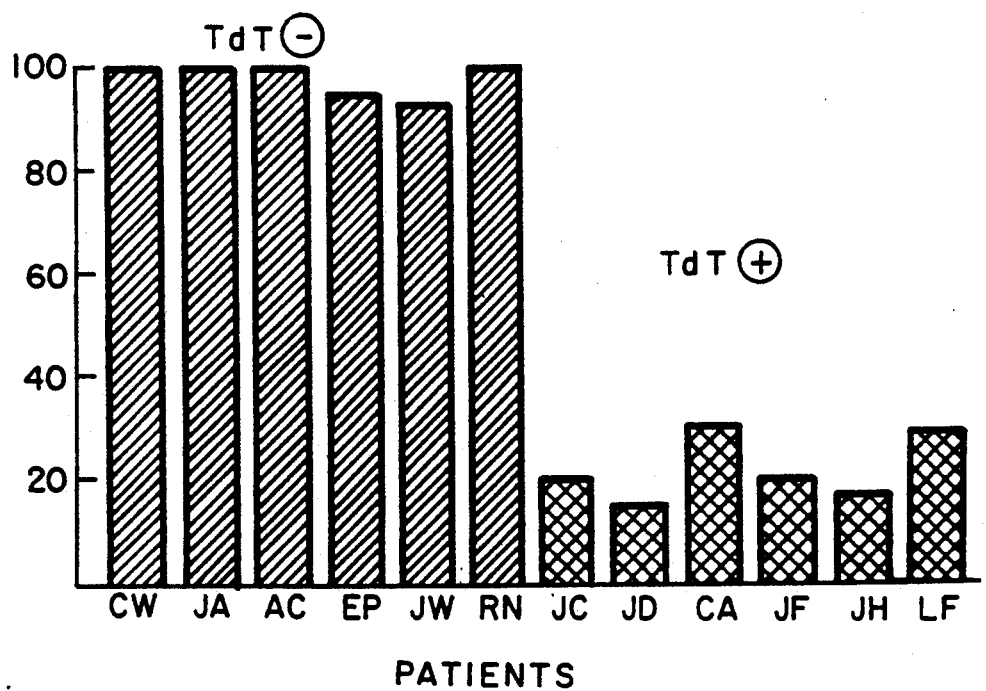
FIG. 6 is a graph illustrating the effects of 2', 3'-dideoxyadenosine and coformycin on freshly collected leukemia cells from human subjects.

Experimentally, all twelve fresh leukemia cell cultures were continuously exposed ex-vivo to 250 uM of ddA and 30 uM of CF for 72 hours. Each was then individually evaluated for viability as determined by trytan blue staining. The empirical results are illustrated by FIG. 6. Each result expressed represents the percent of control viability for each sample. Each determination represents the mean of triplicate flasks.

As shown by FIG. 6, the cultured blast cells from six patients having TdT-negative acute leukemias were demonstratably resistant to the effects of ddA and CF in combination. In contrast, leukemic blast cultures from those six persons demonstrating TdT-positive acute lymphoblastic leukemia revealed 70–85% cell death as a result of ddA and CF in combination. In two instances, exposure to 30 uM of CF alone had no effect on cell viability. These data thus clearly demonstrate the selective cytotoxic efficacy of the present methodology in killing ex-vivo clinical samples from human patients afflicted with TdT-positive neoplastic diseases.

The present invention is not to be restricted in form nor limited in scope except by the claims appended hereto.

What we claim is:

1. A therapeutic method for treating terminal deoxynucleotidyl transferase-positive leukemias and lymphomas in-situ comprising the step of:
    administering a therapeutic composition to the terminal deoxynucleotidyl transferase-positive cells in-situ, said therapeutic composition comprising a nitrogeneous heterocyclic base selected from the group consisting of purines and purines derivatives, and a dideoxy-pentose monosaccharide moiety.

2. A therapeutic method for treating terminal deoxynucleotidyl transferase-positive leukemias and lymphomas in-site comprising the step of:

administering a therapeutic composition to the terminal deoxynucleotidyl transferase-positive cells in-situ, said therapeutic composition comprising a nitrogeneous heterocyclic base selected from the group consisting of pyrimidines and pyrimidine derivatives, and a dideoxy-pentose monosaccharide moiety.

3. A therapeutic method as recited in claim 1 or 2 wherein said therapeutic composition further comprises a phosphoric acid moiety.

4. A therapeutic method as recited in claim 1 or 2 wherein said administration of said therapeutic composition results in an in-situ concentration of said therapeutic composition ranging from 50–150 micromoles per milliliter of fluid.

5. The therapeutic method as recited in claim 1 or 2 further comprising administering a purine deaminase inhibitor in-situ with said therapeutic composition.

* * * * *